(12) United States Patent
Sahin et al.

(10) Patent No.: US 10,772,511 B2
(45) Date of Patent: Sep. 15, 2020

(54) MOTION SENSOR USING CROSS COUPLING

(71) Applicant: QUALCOMM Incorporated, San Diego, CA (US)

(72) Inventors: Mustafa Emin Sahin, San Diego, CA (US); Udara Fernando, San Diego, CA (US); Seunghwan Kim, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 345 days.

(21) Appl. No.: 15/981,558

(22) Filed: May 16, 2018

(65) Prior Publication Data
US 2019/0350465 A1 Nov. 21, 2019

(51) Int. Cl.
*A61B 5/0205* (2006.01)
*A61B 5/11* (2006.01)
(Continued)

(52) U.S. Cl.
CPC .......... *A61B 5/0205* (2013.01); *A61B 5/1102* (2013.01); *A61B 5/113* (2013.01);
(Continued)

(58) Field of Classification Search
CPC .......... A61B 5/00; A61B 5/02; A61B 5/0205; A61B 5/05; A61B 5/1126; A61B 5/1102;
(Continued)

(56) References Cited

U.S. PATENT DOCUMENTS

| | | | | |
|---|---|---|---|---|
| 5,227,800 A | * | 7/1993 | Huguenin | G01S 7/024 250/332 |
| 5,573,012 A | * | 11/1996 | McEwan | A61B 5/024 600/428 |

(Continued)

OTHER PUBLICATIONS

Abdelnasser H., et al., "WiGest: A Ubiquitous WiFi-based Gesture Recognition System," May 18, 2015, 10 pages.
(Continued)

*Primary Examiner* — Peter M Bythrow
(74) *Attorney, Agent, or Firm* — Thien T. Nguyen; Weaver Austin Villeneuve & Sampson LLP

(57) ABSTRACT

Techniques for performing one or both of gesture recognition and biometric monitoring with an electronic device are disclosed, where the electronic device has a wireless communications capability using beamforming techniques and includes a plurality of millimeter wave antenna modules. Each module includes at least one transmit antenna and at least one receive antenna, operable in one or more frequency ranges not less than 20 GHz, the receive antenna coupled with a first branch configured to receive H-polarized signals and a second branch configured to receive V-polarized signals. Performing one or both of gesture recognition and biometric monitoring includes detecting a presence and motion of a reflective object or anatomical feature by determining a relationship between received H-polarized signals and received V-polarized signals for two or more receive antennas as a function of time.

30 Claims, 9 Drawing Sheets

(51) Int. Cl.

| | |
|---|---|
| *A61B 5/113* | (2006.01) |
| *A61B 5/00* | (2006.01) |
| *G06F 3/01* | (2006.01) |
| *G06K 9/00* | (2006.01) |
| *H01Q 21/24* | (2006.01) |
| *H04B 7/10* | (2017.01) |
| *H04W 52/02* | (2009.01) |
| *H04W 64/00* | (2009.01) |
| *H04W 74/08* | (2009.01) |
| *H01Q 21/06* | (2006.01) |

(52) U.S. Cl.
CPC ............ *A61B 5/6897* (2013.01); *G06F 3/017* (2013.01); *G06K 9/00355* (2013.01); *H01Q 21/24* (2013.01); *H04B 7/10* (2013.01); *H04W 52/0216* (2013.01); *H04W 64/006* (2013.01); *H04W 74/0833* (2013.01); *H01Q 21/062* (2013.01); *H01Q 21/065* (2013.01)

(58) Field of Classification Search
CPC ........ A61B 5/113; A61B 5/6897; G06K 9/80; G06F 3/011; G06F 3/017; H04B 7/10; H04N 5/243; G01S 7/415; G01S 13/86; G01S 13/862; G01S 13/865; G01S 13/867; G01S 13/88
See application file for complete search history.

(56) References Cited

U.S. PATENT DOCUMENTS

| | | | | |
|---|---|---|---|---|
| 6,239,736 B1* | 5/2001 | McDonald | ............ | G01S 7/2922 340/554 |
| 6,825,456 B2* | 11/2004 | Chadwick | ............... | G01S 7/025 250/225 |
| 6,967,612 B1* | 11/2005 | Gorman | .................. | G01S 13/34 342/22 |
| 7,391,362 B2* | 6/2008 | Beckner | .................. | G01S 7/024 342/118 |
| 7,916,066 B1* | 3/2011 | Osterweil | ............... | G01S 13/56 342/28 |
| 8,062,220 B2* | 11/2011 | Kurtz | .................. | A61B 5/0064 600/301 |
| 8,115,472 B2* | 2/2012 | Mostov | .................. | G01R 23/16 324/76.21 |
| 8,334,703 B2* | 12/2012 | Mostov | .................. | G01S 7/024 324/637 |
| 8,721,554 B2* | 5/2014 | Lin | ........... | A61B 5/05 600/484 |
| 8,814,805 B2* | 8/2014 | Lin | ........... | A61B 5/05 600/534 |
| 8,823,581 B2* | 9/2014 | Mostov | .................. | G01V 8/005 342/118 |
| 9,000,973 B2* | 4/2015 | Hyde | ...................... | G01S 7/412 340/573.1 |
| 9,335,407 B2* | 5/2016 | Bowring | ................. | G01S 7/024 |
| 10,063,264 B2* | 8/2018 | Crouch | ................. | H04L 27/04 |
| 10,310,621 B1* | 6/2019 | Lien | ..................... | G06F 21/6245 |
| 10,670,700 B2* | 6/2020 | McMahon | ............. | G01S 13/56 |
| 2007/0210960 A1* | 9/2007 | Rofougaran | ............. | H01Q 3/26 342/368 |
| 2008/0316085 A1* | 12/2008 | Rofougaran | .......... | A63F 13/211 342/22 |
| 2010/0152600 A1* | 6/2010 | Droitcour | ............. | A61B 5/1114 600/534 |
| 2011/0181510 A1* | 7/2011 | Hakala | .................... | G06F 3/017 345/158 |
| 2014/0316261 A1* | 10/2014 | Lux | ......................... | G01S 13/56 600/430 |
| 2014/0368378 A1* | 12/2014 | Crain | ...................... | G01S 7/026 342/25 A |
| 2015/0301167 A1* | 10/2015 | Sentelle | ................ | G01S 13/888 342/22 |
| 2016/0206244 A1* | 7/2016 | Rogers | ................. | A61B 5/7275 |
| 2016/0370463 A1 | 12/2016 | Schwager et al. | | |
| 2017/0097413 A1 | 4/2017 | Gillian et al. | | |
| 2018/0062256 A1* | 3/2018 | Kim | ....................... | H01Q 21/08 |
| 2019/0058264 A1* | 2/2019 | Jung | ...................... | H01Q 1/243 |

OTHER PUBLICATIONS

Saxena N., et al., "Still and Silent: Motion Detection for Enhanced RFID Security and Privacy without Changing the Usage Model", RFIDSec 2010: Radio Frequency Identification: Security and Privacy Issues, 2010, 20 pages.
International Search Report and Written Opinion—PCT/US2019/031572—ISA/EPO—dated Jul. 11, 2019.

* cited by examiner

MOTION SENSOR USING CROSS COUPLING

TECHNICAL FIELD

This disclosure relates to motion sensing techniques, and more particularly to using transmit and receive communication antennas of an electronic device for motion sensing.

DESCRIPTION OF THE RELATED TECHNOLOGY

Electronic devices such as smart phones, tablets, or "Internet of Things" (IoT) devices and appliances can be made more functional by equipping them with motion sensors configured to support gesture recognition and/or biometric monitoring. For example, gesture recognition enables users to perform certain functions by swiping a hand, finger, or stylus proximate to but not necessarily in contact with the electronic device. Potential uses include: turning the device on/off, turning the volume up/down, flipping a page, scrolling a page up/down, for example. Gesture recognition may be particularly useful when the device does not have a touch screen or when touching the screen is inconvenient (e.g. wet hands). Motion sensors contemplated by the present disclosure may also be configured to detect very small motions and can be used for biometric monitoring and measurements, such as (heartbeat rate and respiratory rate).

In the absence of the presently disclosed techniques, touch or gesture recognition sensors used in electronic devices are generally capacitive sensing, infra-red (IR) motion detectors, or cameras with video processing. Capacitive sensing and IR detection require dedicated hardware that are relatively bulky; video processing of camera imagery is a very inefficient method in terms of power consumption and computational requirements since it needs continuous monitoring and processing.

Thus, improved motions sensing techniques are desirable.

SUMMARY

The systems, methods and devices of this disclosure each have several innovative aspects, no single one of which is solely responsible for the desirable attributes disclosed herein.

One innovative aspect of the subject matter described in this disclosure relates to sensing motion proximate to an electronic device or appliance using RF components disposed on the device. The RF components include a plurality of mm wave antenna modules, each module including at least one transmit and one receive antenna, operable at a frequency of 20 GHz or higher. The RF components may be compatible with fifth generation New Radio (5G NR) communications standards. The RF components are utilized for motion sensing at a low duty cycle of about 10 microseconds per 100 milliseconds, when they are normally not used for 5G NR communications.

According to some implementations, a method includes performing one or both of gesture recognition and biometric monitoring with an electronic device, the electronic device having a wireless communications capability using beamforming techniques and including a plurality of millimeter wave antenna modules, each module including at least one transmit antenna and at least one receive antenna, operable in one or more frequency ranges not less than 20 GHz, the receive antenna coupled with a first branch configured to receive H-polarized signals and a second branch configured to receive V-polarized signals. The performing one or both of gesture recognition and biometric monitoring includes detecting a presence and motion of a reflective object or anatomical feature by determining a relationship between received H-polarized signals and received V-polarized signals for two or more receive antennas as a function of time.

In some examples, the antenna modules may be compatible with 5G wireless communications standards.

In some examples, the antenna modules may include one or both of patch and dipole antennas.

In some examples, the reflective object may be one or more of a hand or other appendage of a user, or a hand held object.

In some examples, the motion of the anatomical feature may be related to one or both of respiration and heartbeat and the biometric monitoring may include monitoring one or both of the respiration and the heartbeat.

In some examples, the performing one or both of gesture recognition and biometric monitoring may include transmitting a low power signal from the at least one transmit antenna and the received H-polarized signals and received V-polarized signals result from cross coupling between the transmit antenna and the receive antenna. In some examples, power of the low power signal may be not greater than 5 milliwatts. In some examples, the low power signal may be synchronized to occur only within random access channel slots. In some examples, the low power signal may be transmitted at a duty cycle of less than 0.01%. In some examples, the low power signal may be periodically transmitted during intervals approximately 100 msec apart, each interval having a duration of less than 10 microseconds.

According to some implementations, an apparatus includes a processor and an electronic device having a wireless communications capability using beamforming techniques and including a plurality of millimeter wave antenna modules, each module including at least one transmit antenna and at least one receive antenna, operable in one or more frequency ranges not less than 20 GHz, the receive antenna coupled with a first branch configured to receive H-polarized signals and a second branch configured to receive V-polarized signals. The processor is configured to perform one or both of gesture recognition and biometric monitoring with the electronic device by detecting a presence and motion of a reflective object or anatomical feature by determining a relationship of received H-polarized signals and received V-polarized signals as a function of time.

In some examples, the antenna modules may be compatible with 5G wireless communications standards.

In some examples, the antenna modules may include one or both of patch and dipole antennas.

In some examples, the reflective object may be one or more of a hand or other appendage of a user, or a hand held object.

In some examples, the motion of the anatomical feature may be related to one or both of respiration and heartbeat and the biometric monitoring may include monitoring one or both of the respiration and the heartbeat.

In some examples, the received H-polarized signals and received V-polarized signals may result from cross coupling, of a low power signal transmitted from the at least one transmit antenna, between the transmit antenna and the receive antenna. In some examples power of the low power signal may be not greater than 5 milliwatts. In some examples, the low power signal may be synchronized to occur only within random access channel slots. In some examples, the low power signal may be transmitted at a duty cycle of less than 0.01%. In some examples, the low power signal may be periodically transmitted during intervals approximately 100 msec apart, each interval having a duration of less than 10 microseconds.

According to some implementations, a non-transitory computer readable medium stores program code to be executed by a processor, the program code comprising instructions configured to cause the processor to: perform one or both of gesture recognition and biometric monitoring with an electronic device, the electronic device having a wireless communications capability using beamforming techniques and including a plurality of millimeter wave antenna modules, each module including at least one transmit antenna and at least one receive antenna, operable in one or more frequency ranges not less than 20 GHz, the receive antenna coupled with a first branch configured to receive H-polarized signals and a second branch configured to receive V-polarized signals. The processor detects a presence and motion of a reflective object or anatomical feature by determining a relationship of received H-polarized signals and received V-polarized signals for two or more receive antennas as a function of time.

In some examples, the reflective object may be one or more of a hand or other appendage of a user, or a hand held object.

In some examples, the motion of the anatomical feature may be related to one or both of respiration and heartbeat and the biometric monitoring includes monitoring one or both of the respiration and the heartbeat.

In some examples, the received H-polarized signals and received V-polarized signals may result from cross coupling, of a low power signal transmitted from the at least one transmit antenna, between the transmit antenna and the receive antenna. In some examples, power of the low power signal may be not greater than 5 milliwatts. In some examples, the low power signal may be transmitted at a duty cycle of less than 0.01%. In some examples, the low power signal may be synchronized to occur only within random access channel slots.

According to some implementations, an apparatus includes an electronic device having a wireless communications capability using beamforming techniques and including a plurality of millimeter wave antenna modules, each module including at least one transmit antenna and at least one receive antenna, operable in one or more frequency ranges not less than 20 GHz, the receive antenna coupled with a first branch configured to receive H-polarized signals and a second branch configured to receive V-polarized signals, and means for performing one or both of gesture recognition and biometric monitoring with the electronic device by detecting a presence and motion of a reflective object or anatomical feature by determining a relationship of received H-polarized signals and received V-polarized signals as a function of time.

In some examples, the received H-polarized signals and received V-polarized signals may result from cross coupling, of a low power signal transmitted from the at least one transmit antenna, between the transmit antenna and the receive antenna. In some examples, power of the low power signal may be not greater than 5 milliwatts and the low power signal is synchronized to occur only within random access channel slots.

BRIEF DESCRIPTION OF THE DRAWINGS

Details of one or more implementations of the subject matter described in this specification are set forth in this disclosure and the accompanying drawings. Other features, aspects, and advantages will become apparent from a review of the disclosure. Note that the relative dimensions of the drawings and other diagrams of this disclosure may not be drawn to scale. The sizes, thicknesses, arrangements, materials, etc., shown and described in this disclosure are made only by way of example and should not be construed as limiting. Like reference numbers and designations in the various drawings indicate like elements.

DETAILED DESCRIPTION

Figure 2:
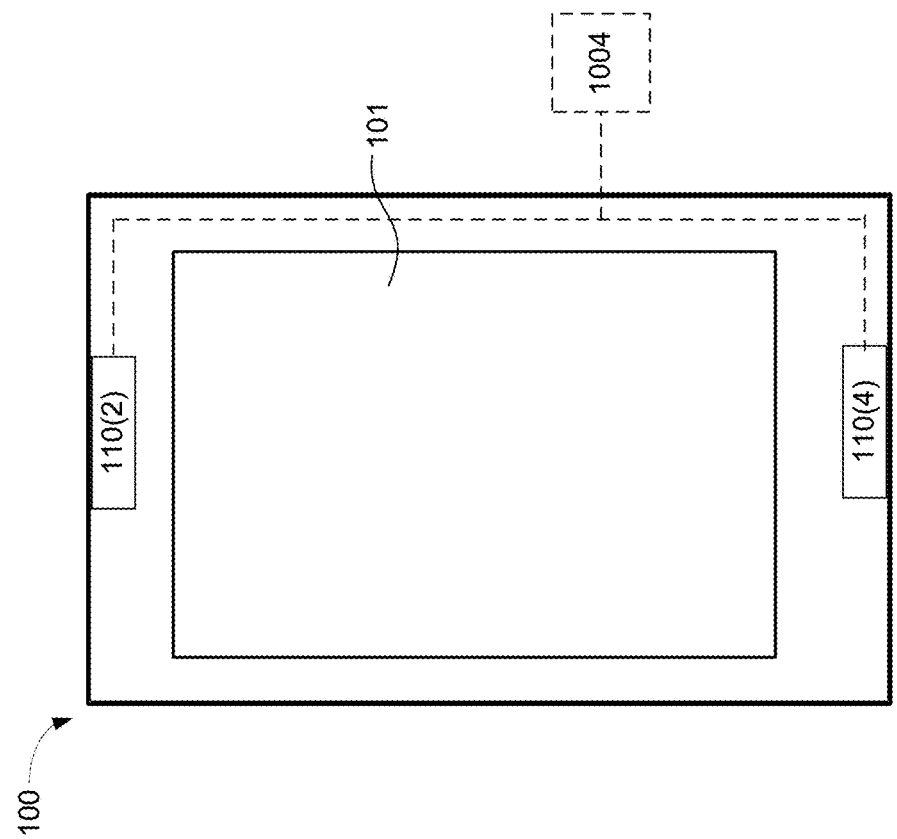
FIG. 2 illustrates a simplified block diagram of the electronic device, according to an implementation.

The following description is directed to certain implementations for the purposes of describing the innovative aspects of this disclosure. However, a person having ordinary skill in the art will readily recognize that the teachings herein may be applied in a multitude of different ways. The described implementations may be implemented in any device, apparatus, or system that includes a millimeter band communications capability. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands and patches, etc., Bluetooth® devices, personal data assistants (PDAs), wireless electronic mail receivers, hand-held or portable computers, netbooks, notebooks, smartbooks, tablets, printers, copiers, scanners, facsimile devices, global positioning system (GPS) receivers/navigators, cameras, digital media players (such as MP3 players), camcorders, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, steering wheels, camera view displays (such as the display of a rear view camera in a vehicle), electronic photographs, electronic billboards or signs, projectors, architectural structures, microwaves, refrigerators, stereo systems, cassette recorders or players, DVD players, CD players, VCRs, radios, portable memory chips, washers, dryers, washer/dryers, automated teller machines (ATMs), parking meters, packaging (such as in electromechanical systems (EMS) applications including microelectromechanical systems (MEMS) applications, as well as non-EMS applications), aesthetic structures (such as display of images on a piece of jewelry or clothing) and a variety of EMS devices. The teachings herein also may be used in applications such as, but not limited to, electronic switching devices, radio frequency filters, sensors, accelerometers, gyroscopes, motion-sensing devices, magnetometers, inertial components for consumer electronics, parts of consumer electronics products, varactors, liquid crystal devices, electrophoretic devices, drive schemes, manufacturing processes and electronic test equipment. Thus, the teachings are not intended to be limited to the implementations depicted solely in the Figures, but instead have wide applicability as will be readily apparent to one having ordinary skill in the art.

The present inventors have appreciated that transmit/receive antenna modules, operating in the millimeter band (20-300 GHz), that may normally be manifested on a 5G NR wireless device, may be configured to provide a motion detection capability that can be adapted for gesture recognition and/or biometric monitoring.

Figure 1:
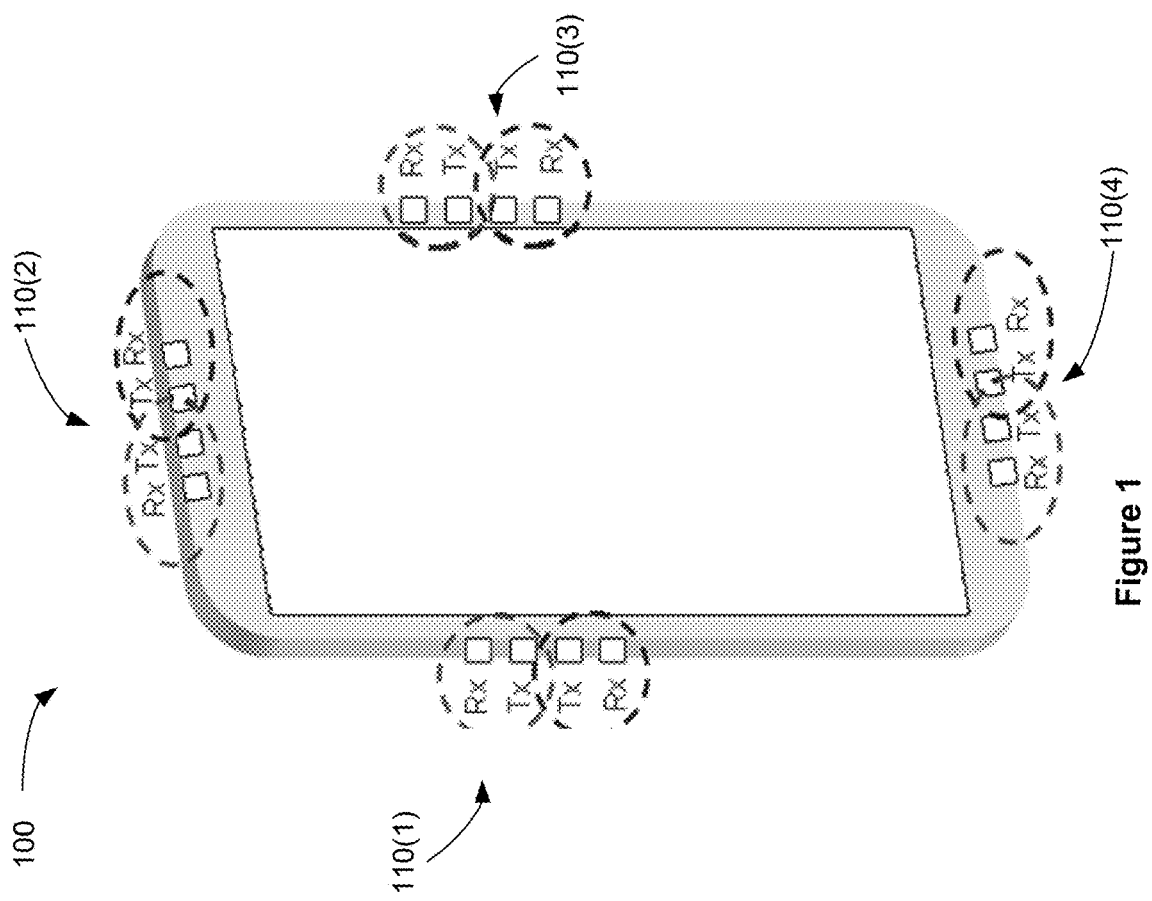
FIG. 1 illustrates an example of an electronic device in which some aspects of this disclosure may be implemented.

FIG. 1 illustrates an example of an electronic device in which some aspects of this disclosure may be implemented.

The illustrated electronic device 100 may be a smart phone, tablet computer, or any item of user equipment configured for wireless connectivity with a network by way of a number of antenna modules. Advantageously, the wireless connectivity may be compatible with a 5G NR or later wireless communication standard, operable at frequencies of 20 GHz and higher and utilizing beam forming techniques such as, for example, multiple-input and multiple-output (MIMO) technology. The example electronic device includes four antenna modules 110 (110(1), 110(2), 110(3) and 110(4)) for providing the wireless connectivity, each antenna module 110 including a 1×4 array of patch or dipole receive (Rx) antennas and transmit (Tx) antennas, but other configurations are within the contemplation of the present disclosure.

FIG. 2 illustrates a simplified block diagram of the electronic device, according to an implementation. For clarity of illustration, antenna modules 110(1) and 110(3) have been omitted from the block diagram of FIG. 2. The electronic device 100 may include a front surface that includes a viewing area 101. The antenna modules 110 may output, to a processor 1004, signal characteristics. The processor 1004 may be communicatively coupled with the antenna modules 110 and with other elements of the electronic device 100. In some implementations, the processor 1004 may be an integral part of the electronic display 100. In other implementations, as suggested by FIG. 1, the processor 1004 may be configured separately from the electronic display 100. In some implementations, the processor may be remotely located in, for example, a remote server.

In some implementations, the processor 1004 may be configured to recognize, from the signal characteristics received from the antenna modules, one or both of a presence and motion of a reflective object (not illustrated). Viewing area 101 may be or include an electronic display, and the processor 1004 may be configured to control the electronic display responsive to recognized motions of the reflective object, as described in more detail hereinbelow.

Figure 3:
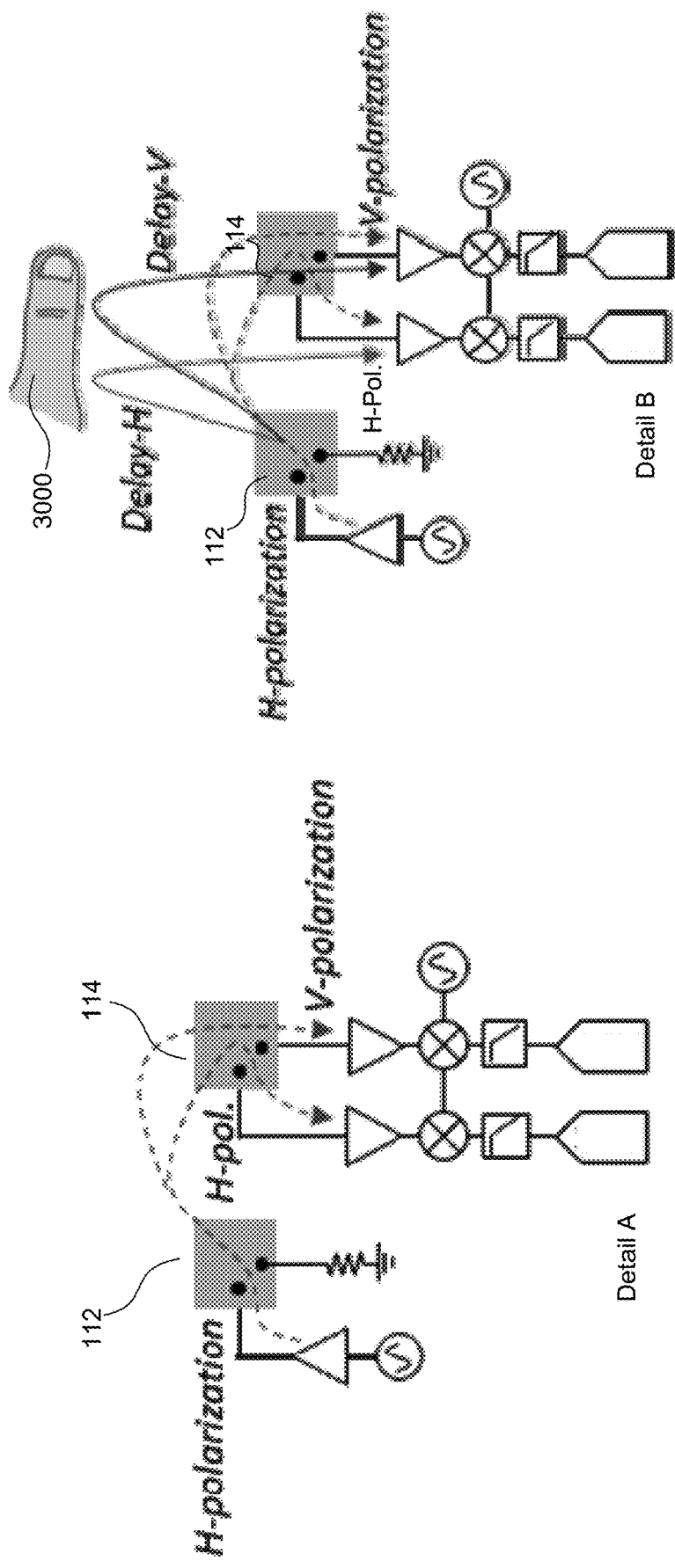
FIG. 3 illustrates cross coupling between a transmit antenna and a receive antenna, according to an implementation.

A signal from a Tx antenna may have a significant cross coupling to one or more Rx antennas, at least for mm wave signaling using patch/dipole antennas. FIG. 3 illustrates cross coupling between a Tx antenna 112 and a Rx antenna 114. Each of the Tx antenna 112 and the Rx antenna 114 may be included in an antenna module 110.

In some implementations, the signals from the Tx antenna may be 5G NR uplink signals such as Physical Uplink Control Channel (PUCCH) signals, Physical Uplink Shared Channel (PUSCH) signals, Random Access Channel (RACH) signals, sounding reference signals (SRS) or continuous wave (CW) signals. Advantageously, the signals may be transmitted at a low power (less than 5 milliwatts, for example) several times per second with a duty cycle of 0.01% or less. For example, the signals may be transmitted at intervals of 0.1 sec, in pulses having a duration of 10 microseconds or less. In some implementations, timing of the low power signals is synchronized to occur only within random access channel slots.

In the illustrated example, the Rx antenna 114 includes H and V polarized branches. The present inventors have found that a relationship between the H and V polarized signals received by the respective branches (e.g., a ratio Rx_H/Rx_V) may be used as an indicator of presence or absence of a reflective object. More particularly, referring to Detail A, when no reflective object is proximate to the electronic device, the ratio Rx_H/Rx_V may have a first value. In the presence of a reflective object 3000 proximate to (in the near field of) the Tx antenna 112, Detail B, the relationship changes significantly as a result of signals coupled to the H and V paths being perturbed differently.

This phenomenon may be exploited to detect not only proximity of a reflective object, but motion as well. As a result, transmit/receive antenna modules, may be used as motion detectors. Where the electronic device, even in the absence of the disclosed techniques, would ordinarily include two or more antenna modules for beamforming, a gesture recognition capability and/or a biometric measurement capability may thus be obtained using those antenna modules while adding minimal additional hardware and cost to the electronic device.

Figure 4:
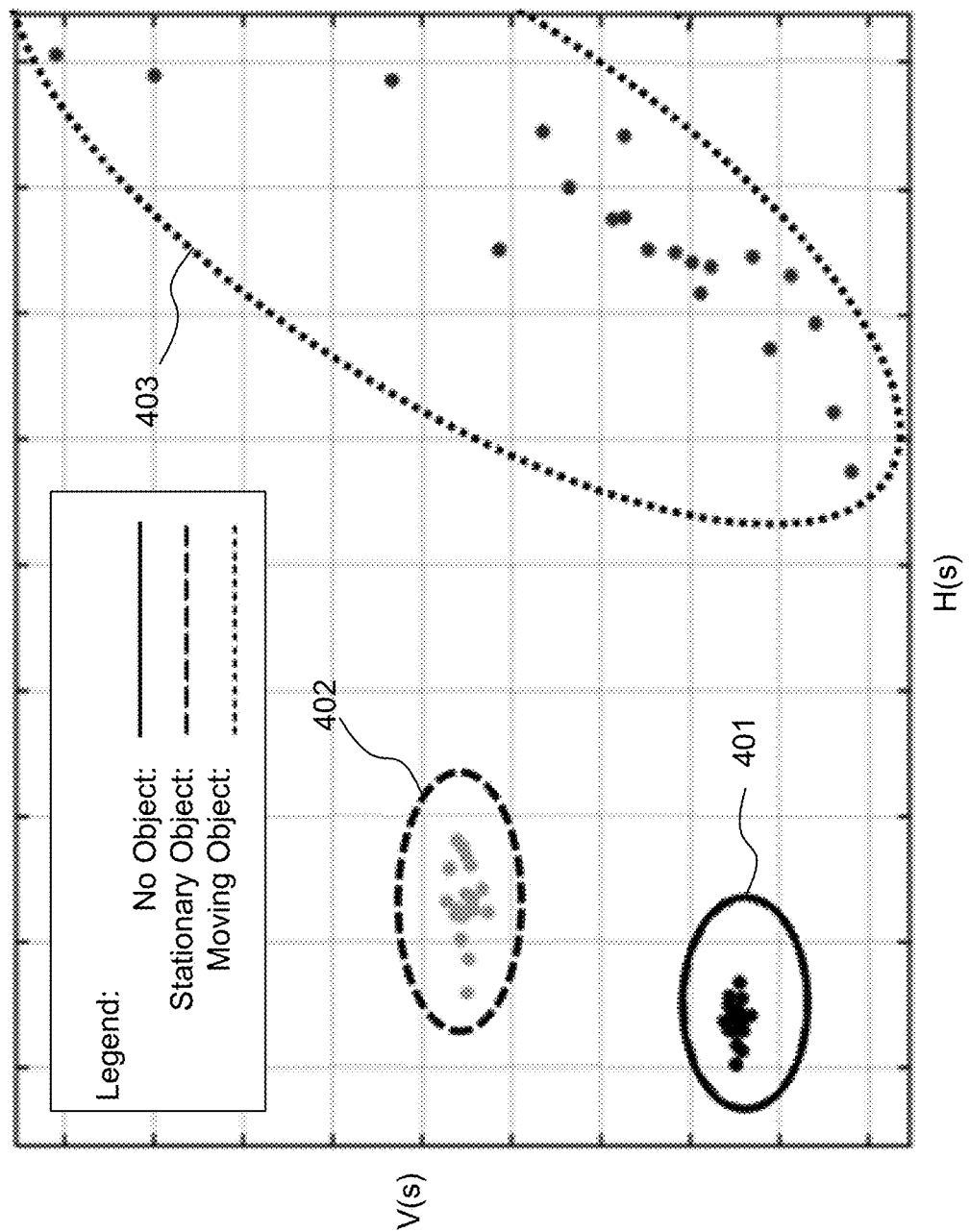
FIG. 4 illustrates an example of the effect of an object on the relationship of received H and V polarized signals according to an implementation.

FIG. 4 illustrates an example of the effect of an object on the relationship of Rx_H to Rx_V by depicting a map of measured received strength of H-polarized (H(s)) and V-polarized (V(s)) polarized signals. It may be observed that, in the absence of a reflective object, the relationship of Rx_H to Rx_V, more particularly, the ratio Rx_H/Rx_V, as measured during a time interval, is relatively constant, i.e., the mapped points are clustered relatively tightly in a region 401. In the presence of a reflective object 3000, the ratio of Rx_H/Rx_V, as measured during a similar time interval, is also relatively constant, i.e., the measured points are clustered relatively tightly in a region 402, but the region 402 is centered at a distinctly different ratio of Rx_H/Rx_V. When the reflective object is in motion, the Rx_H/Rx_V ratio demonstrates significant temporal variation, i.e., the measured points are widely scattered within a region 403, when measured during the similar time interval, as well as being centered at yet a different ratio of Rx_H/Rx_V. As a result, presence of a moving object may be detected by a single antenna receiver and distinguished both from absence of a reflective object, and from presence of a stationary object.

Figure 5:
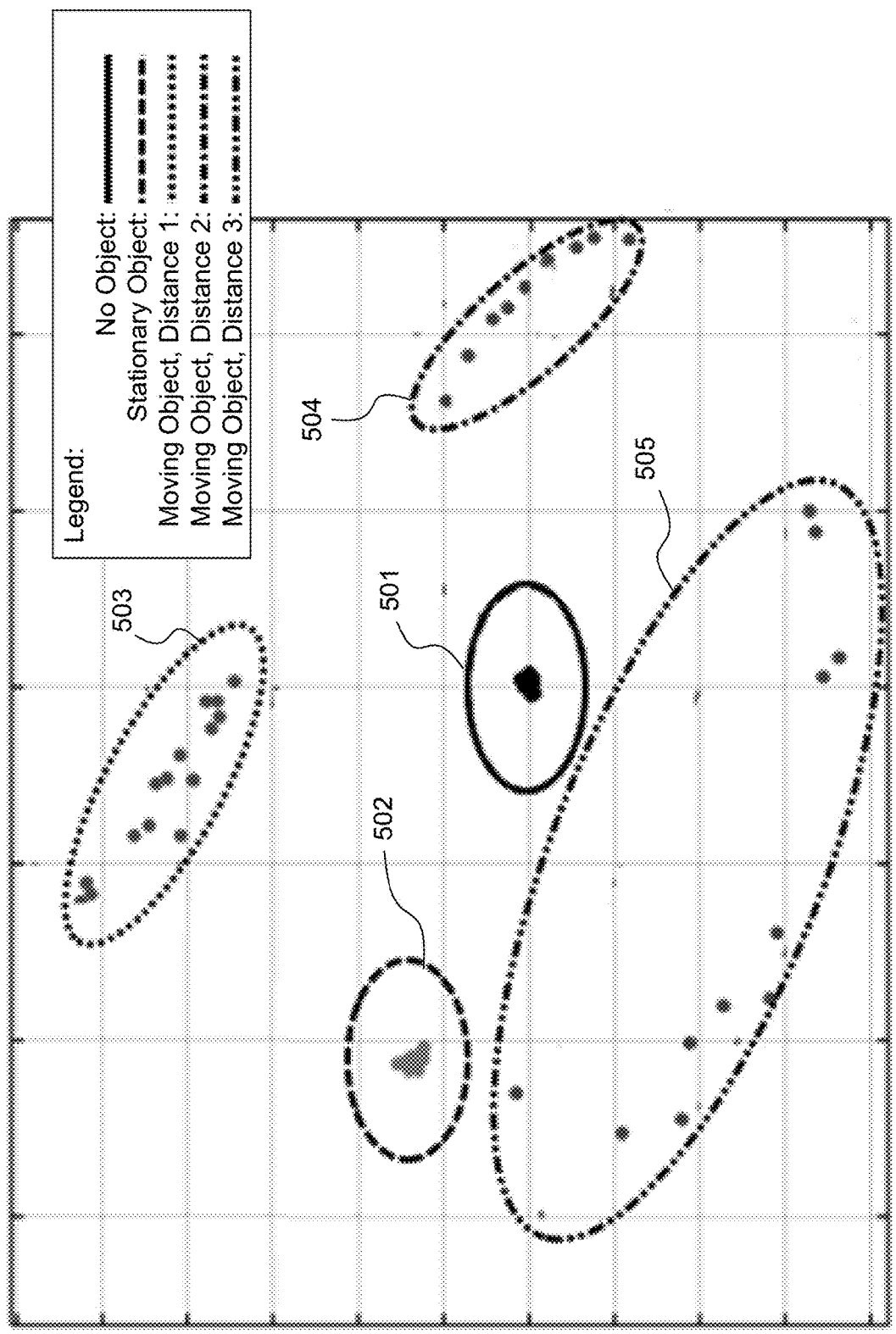
FIG. 5 illustrates another example of the effect of an object on the relationship of received H and V polarized signals.

FIG. 5 illustrates another example of the effect of an object on the ratio of Rx_H/Rx_V by depicting a map of measured received strength of H-polarized (H(s)) and V-polarized (V(s)) polarized signals. As indicated above in connection with FIG. 5, in the absence of a reflective object the ratio of Rx_H/Rx_V is relatively constant, i.e., the measured points are clustered relatively tightly in region 501. In the presence of a reflective object, the ratio of Rx_H/Rx_V is still fairly constant, but the region 502 is centered at a distinctly different ratio of Rx_H/Rx_V. When the reflective object is in motion, the Rx_H/Rx_V ratio demonstrates significant variation, i.e., the measured points are widely scattered, as well as being centered at yet a different ratio of Rx_H/Rx_V. FIG. 5 further illustrates an effect of distance of the object from the electronic device on the ratio of Rx_H/Rx_V. It may be observed that each of region 503, corresponding to a first distance, region 504 corresponding to a fourth distance, and region 505, corresponding to a fifth distance exhibit similar scattering, but are centered at different locations on the map.

The present inventors have appreciated that, in view of the above-described phenomenon, an electronic device may be configured to recognize motion of a reflective object. At least when the electronic device includes two or more separately disposed pairs of Tx/Rx antennas, characteristics of the motion, including direction and rate, may be obtained. By appropriate tuning, sensitivity to motions of various scales may be obtained. For example, in some implementations, location and direction of "gestures" may be recognized, the gestures being, for example, movement of a user's hand or other appendage or hand held object over a distance in the range of 0.1-10 inches. In some implementations, gesture recognition may be used to provide control inputs to the electronic device. In other implementations, smaller scale motions may be detected. For example, the electronic device may be tuned to be sensitive to motions in the range of 0.01-0.5 inches. In such implementations, the disclosed techniques may be used for biometric monitoring to detect or measure respiration or heartbeat rate of a user or patient.

Figure 6:
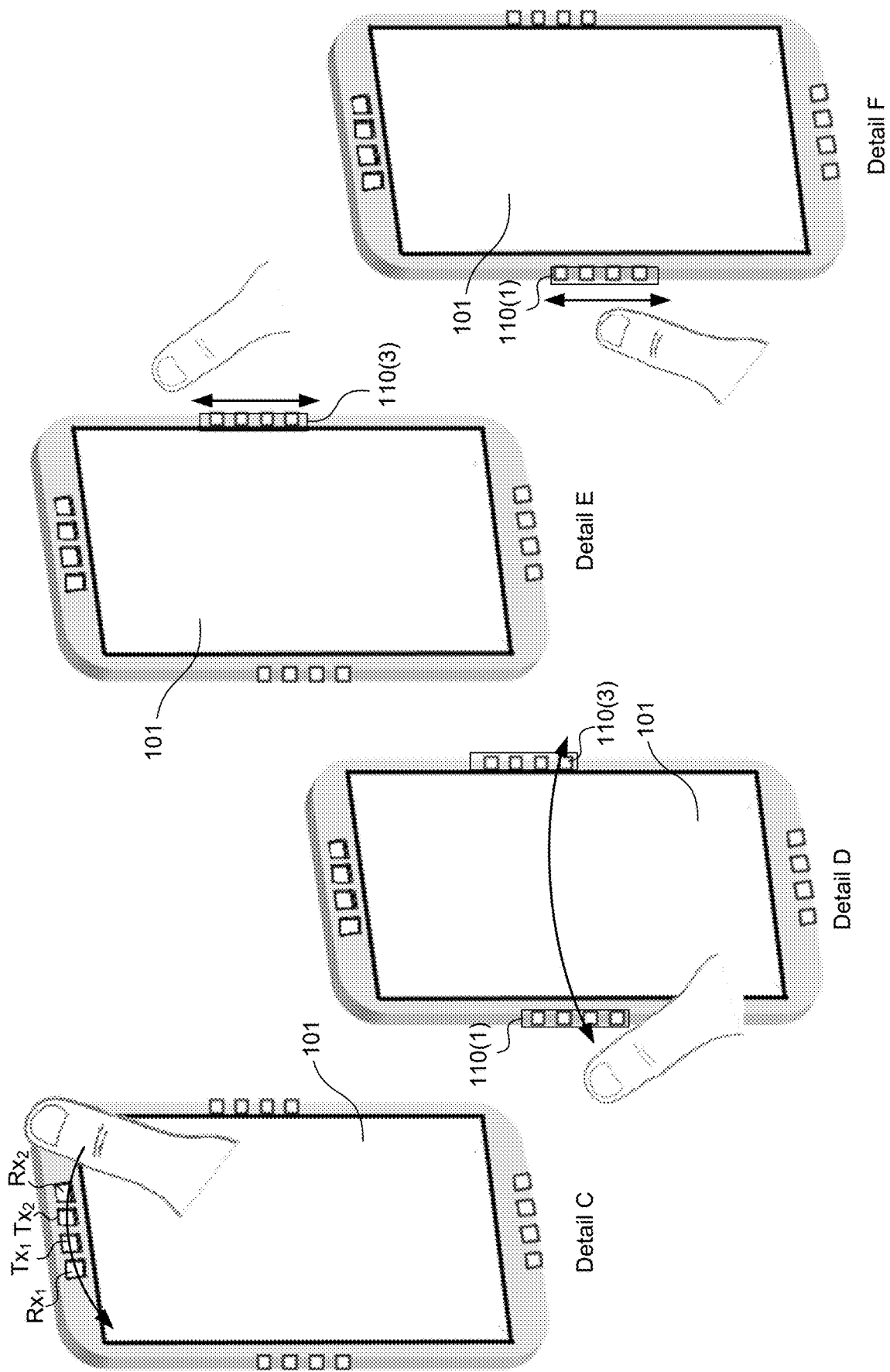
FIG. 6 illustrates some examples of how the disclosed techniques may be used to provide user control inputs to an electronic device, including a display.

FIG. 6 illustrates some examples of how the disclosed techniques may be used to provide user control inputs to an electronic device, including a display. The electronic device may be a portable device such as a tablet, smart phone or smart watch, in some implementations. In other implementations, the electronic device may be wall mounted (e.g., a thermostat control, or an advertising/shopping display), mounted to an appliance (e.g., refrigerator, stove or dishwasher) or be incorporated in a kiosk, user terminal or work station. The electronic device includes a plurality of Rx and Tx antennas as described above and may include or be coupled with a processor coupled with at least the Rx antennas. The processor may be configured to receive, from the Rx antennas, respective Rx_H and Rx_V signals cross coupled from a Tx antenna. By analysis of temporally varying signal strengths of Rx_H relative to Rx_V signals for signals received from two or more separately disposed pairs of Tx and Rx antennas, the processor may determine the presence and direction of motion of a reflective object, such as a user's appendage or hand held object such as a stylus.

In some implementations, for example, referring to Detail C a swiping gesture proximate to antenna module 110(1) may be recognized by the processor as a user command to turn on or turn off a portion or all of a display in viewing area 101. The processor may recognize the gesture as a result of analyzing cross coupled signals received by receive antennas $R_{x1}$ and $R_{x2}$. As a further example, referring now to Detail D, a swiping gesture between antenna modules 110(1) and 110(3) may be recognized by the processor as a user command to flip a page displayed in viewing area 101. The processor may recognize the gesture as a result of analyzing cross coupled signals received by receive antennas that are part of antenna modules 110(1) and 110(3). Similarly, referring to Detail E, a swiping gesture proximate to antenna module 110(3) may be recognized by the processor as a user command to scroll content displayed in viewing area 101 up or down. As a yet further example, referring to Detail F, a swiping gesture proximate to antenna module 110(1) may be recognized by the processor as a user command to increase or decrease speaker volume of the electronic device.

Figure 7:
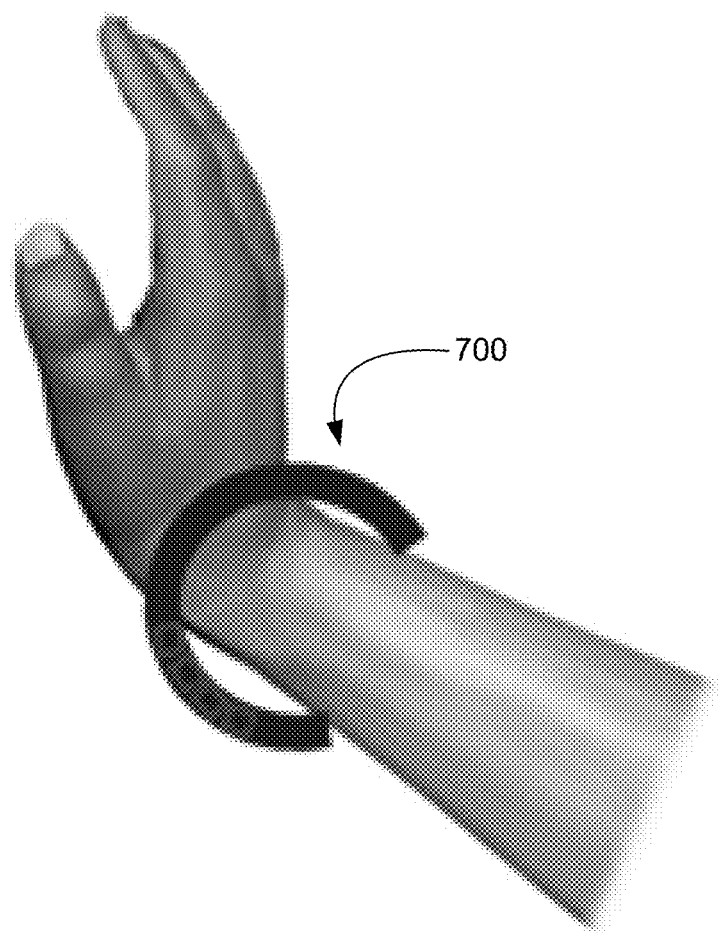
FIG. 7 illustrates examples of how the disclosed techniques may be used to provide biometric monitoring.

FIG. 7 illustrates examples of how the disclosed techniques may be used to provide biometric monitoring. An electronic device 700 may be configured as a wearable device such as a smart watch or activity tracker. The electronic device may include two or more separately disposed pairs of Tx/Rx antennas (not illustrated). The electronic device 700 may be tuned to be sensitive to motions as small as 0.01 inches and be used for biometric monitoring of an anatomical feature of a person wearing the device. For example, the electronic device 700 may be tuned to detect or measure small motions of a wearer's skin resulting from heartbeat, and thereby determine the wearer's pulse rate. As a further example, it will be appreciated that a wearable electronic device may be configured as a chest strap or patch and tuned to be sensitive to motions in the range 0.1-0.5 inches, for example, for purposes of measuring respiration rates. Such electronic devices may be tailored for use in clinical and/or athletic settings, for example.

Figure 8:
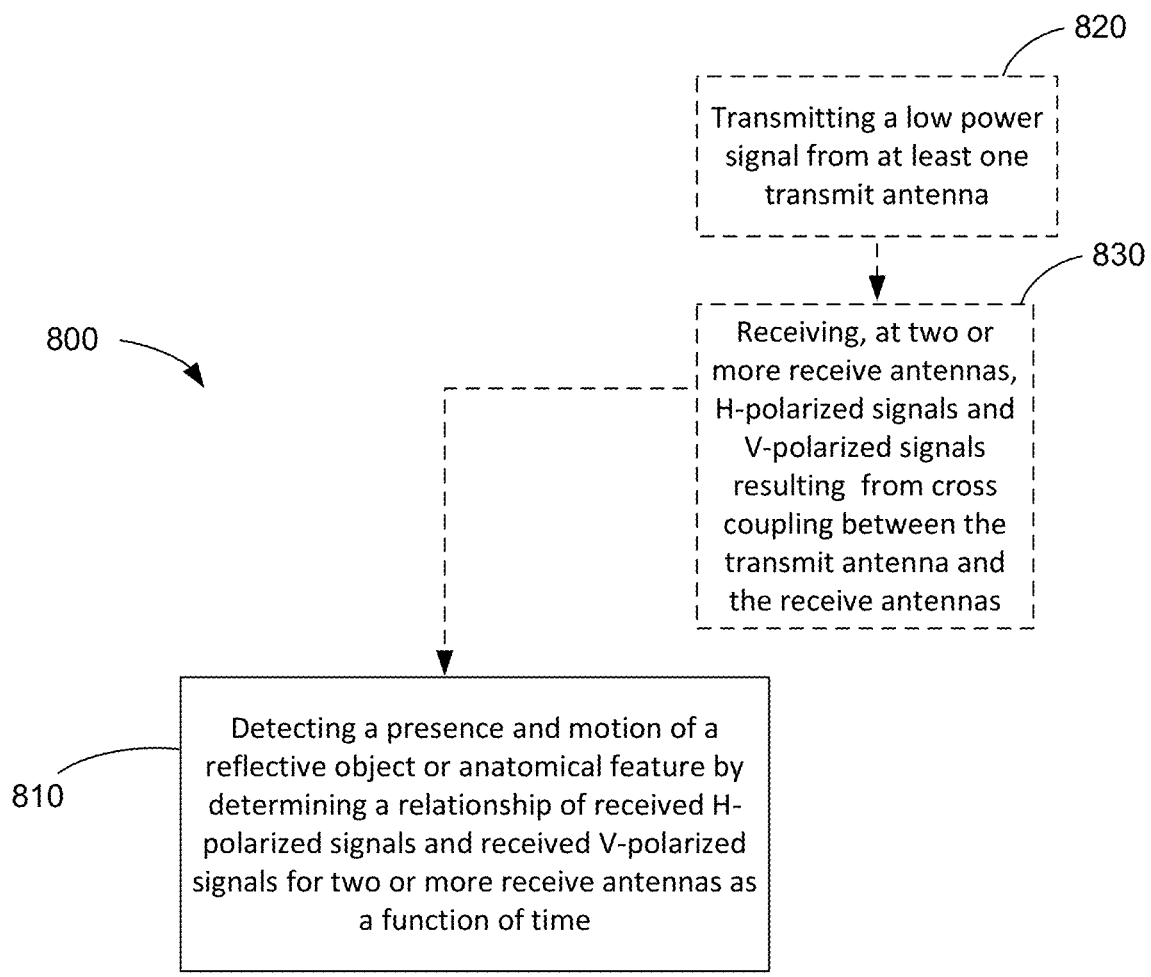
FIG. 8 illustrates an example of a process flow for sensing motion of a reflective object with an electronic device, according to an implementation.

FIG. 8 illustrates an example of a process flow for sensing motion of a reflective object with an electronic device. As described hereinabove, the electronic device may provide a wireless communications capability using beamforming techniques. The electronic device may include a plurality of millimeter wave antenna modules, each module including at least one transmit antenna and at least one receive antenna, operable in one or more frequency ranges not less than 20 GHz, the receive antenna coupled with a first branch configured to receive H-polarized signals and a second branch configured to receive V-polarized signals. The method 800 includes a block 810 of detecting a presence and motion of a reflective object or anatomical feature by determining a relationship between received H-polarized signals and received V-polarized signals for two or more receive antennas as a function of time.

In some implementations, step 810 is preceded by transmitting, at step 820, a low power signal from at least one transmit antenna, and receiving, at step 830, at two or more receive antennas, the H-polarized signals and the V-polarized signals, the H-polarized signals and the V-polarized signals resulting from cross coupling between the transmit antenna and the receive antennas.

Figure 9A:
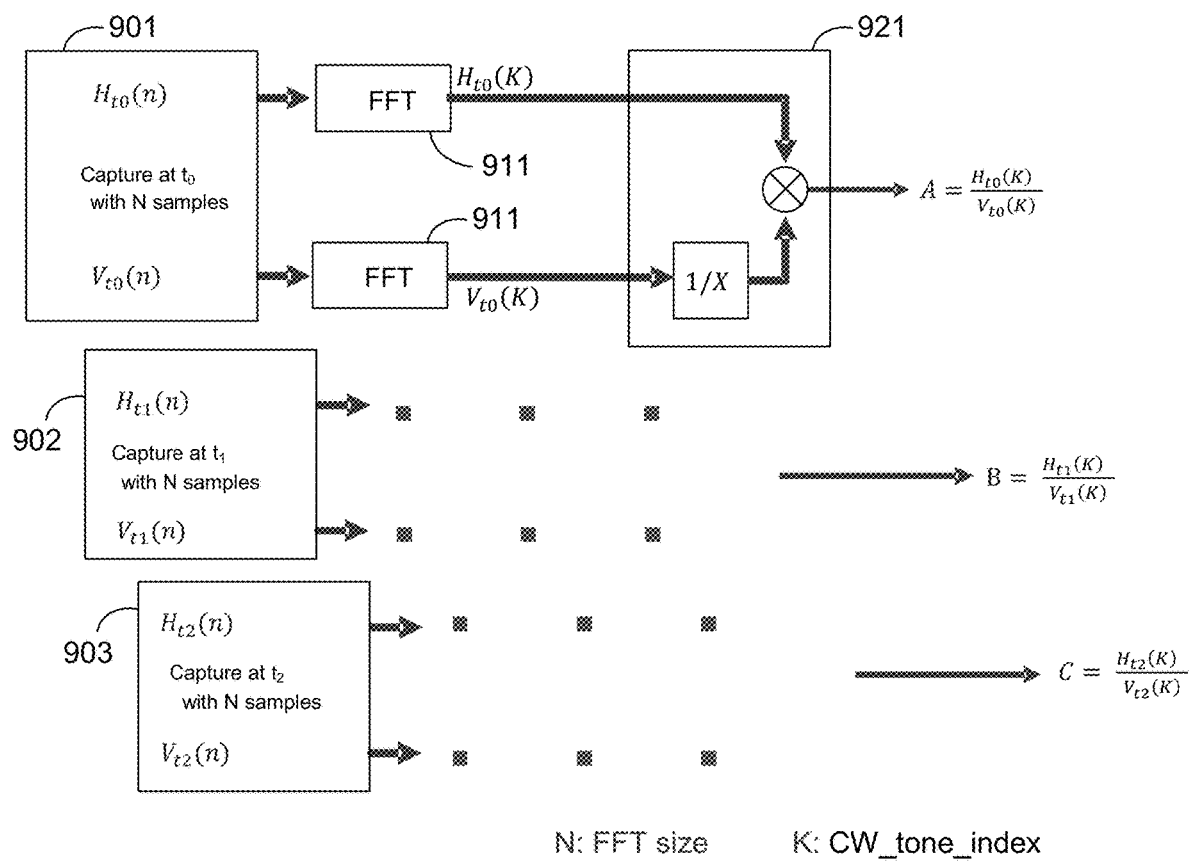
FIGS. 9A and 9B illustrate an example of a method the processor may be configured to execute in order to perform one or both of gesture recognition and biometric monitoring.
Figure 9B:
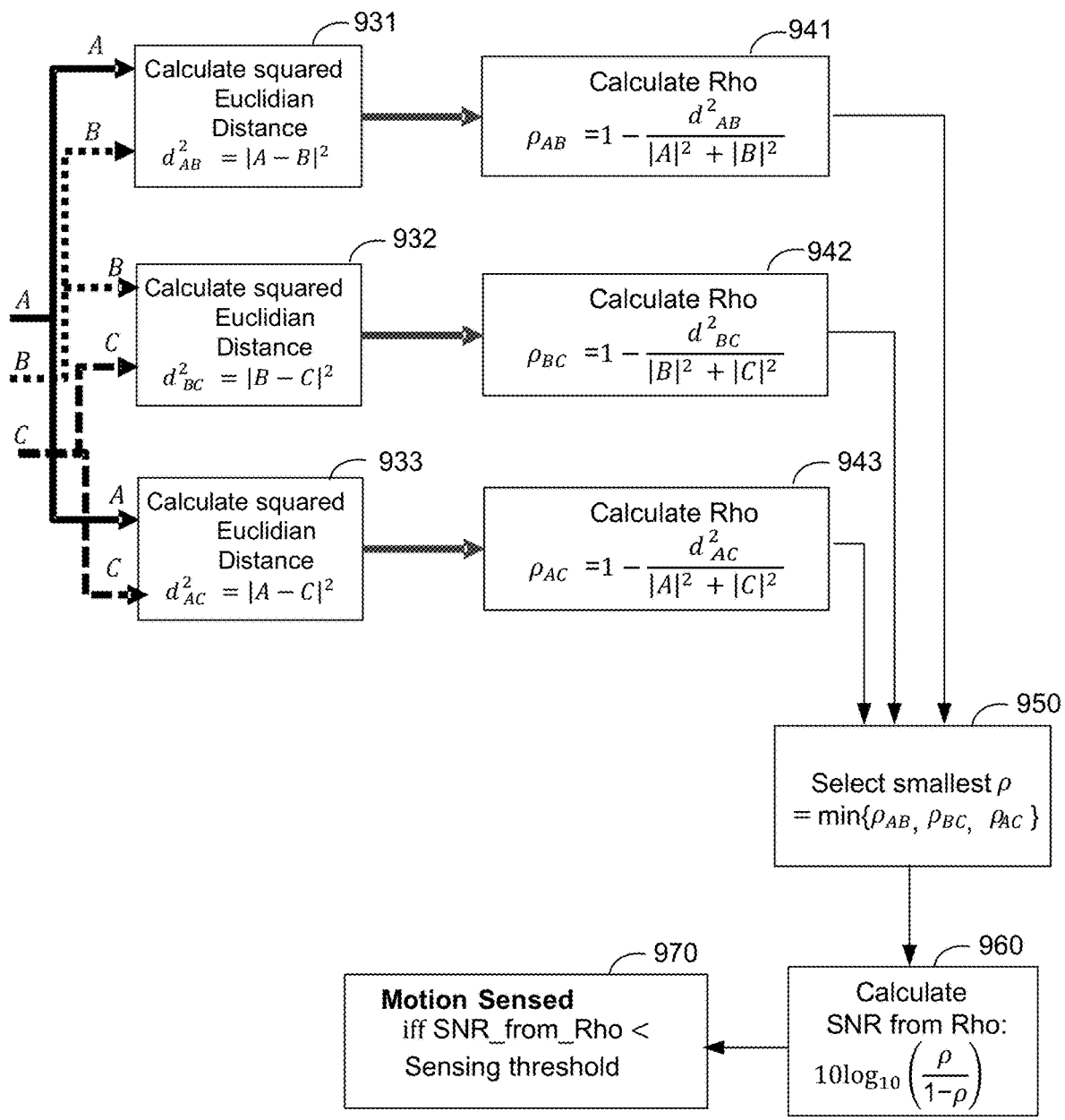

As indicated above, an electronic device may include or be coupled with a processor that is configured to perform one or both of gesture recognition and biometric monitoring with the electronic device by detecting a presence and motion of a reflective object or anatomical feature by determining, as a function of time, a relationship of received H-polarized signals and received V-polarized signals. FIGS. 9A and 9B illustrate an example of a method the processor may be configured to execute in order to perform one or both of gesture recognition and biometric monitoring.

Referring first to FIG. 9A, the processor may receive ("capture"), at discrete time intervals, from one or more Rx antennas, N signal samples of H-polarized signals and V-polarized signals, characterized, respectively, as $H_r(n)$ and $V_r(n)$. In the illustrated example, N samples are captured during three sampling periods during a time $t_0$, during a time $t_1$, and during a time $t_2$. Although three sampling periods are shown in the illustrated implementation, two, four or more sampling periods may be contemplated by the present disclosure. Each sampling period may have a duration of 2-10 microseconds, for example, and be separated by intervals of 0.05 to 0.2 seconds, for example. Where the sampling period is 5 microseconds, and the interval between samples is 0.1 seconds for example, the method may start by capturing a first set of N samples, at block 901, followed by capturing a second set of N samples, approximately 0.1 seconds later, at block 902, followed by capturing a third d set of N samples, approximately 0.1 seconds later, at block 903.

A fast Fourier transform may be executed on each sample $H_r(n)$ and $V_r(n)$ in the first sample set, at block 904 and on each subsequent sample set (FFT process blocks for subsequent sample sets omitted for clarity of illustration). A frequency domain value of $H_r(K)$ and $V_r(K)$ for the captured samples of H-polarized signals and V-polarized signals, resulting from the FFT transform, may be obtained for each sample set, where K, in the illustrated example is a continuous wave (CW) tone index. Next, the processor may determine a relationship between $H_r(K)$ and $V_r(K)$. In the illustrated example, the relationship is a ratio, determined, for the first sample set, at block 921. Other mathematical relationships, for example a difference, may be contemplated, but in the illustrated example, ratios A, B and C are determined for, respectively, the first sample set, the second sample set and the third sample set.

Referring now to FIG. 9B, the ratios A, B and C are used to calculate three respective values of squared Euclidian distances, $d^2_{AB}$ (block 931), $d^2_{BC}$ (block 932), and $d^2_{AC}$ (block 933) and three respective values of ρ (Rho), $\rho_{AB}$ (block 941), $\rho_{BC}$ (block 942) and $\rho_{AC}$ (block 943). Each calculated value of Rho will be between zero and one. Values closer to one indicate little variation in sampled values of Rx_H/Rx_V, thus a decreased likelihood of a moving reflective object. Values closer to zero represent a greater variation in sampled values of Rx_H/Rx_V, thus an increased likelihood of a moving reflective object. Accordingly, the method may proceed, at block 950 with selecting the smallest of $\rho_{AB}$, $\rho_{BC}$, and $\rho_{AC}$. At block 960 a signal to noise (SNR) metric may be calculated, and, at block 970, the processor may make a determination that motion has been sensed if and only if the calculated SNR is less than a criteria (the "sensing threshold") that may be empirically determined. Having made the determination that motion has been sensed, characteristics of the motion, including direction and velocity may be obtained by comparing signals from two or more receive antennas.

Thus, techniques for motion sensing using cross coupling have been disclosed. It will be appreciated that a number of alternative configurations and operating techniques may be contemplated.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor or any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by or to control the operation of data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed to achieve desirable results. Further, the drawings may schematically depict one more example processes in the form of a flow diagram. However, other operations that are not depicted may be incorporated in the example processes that are schematically illustrated. For example, one or more additional operations may be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

What is claimed is:

1. A method comprising:
performing one or both of gesture recognition and biometric monitoring with an electronic device, the electronic device having a wireless communications capability using beamforming techniques and including a plurality of millimeter wave antenna modules, each module including at least one transmit antenna and at least one receive antenna, operable in one or more frequency ranges not less than 20 GHz, the receive antenna coupled with a first branch configured to receive H-polarized signals and a second branch configured to receive V-polarized signals; wherein:
the performing one or both of gesture recognition and biometric monitoring includes detecting a presence and motion of a reflective object or anatomical feature by determining a relationship between received H-polarized signals and received V-polarized signals for two or more receive antennas as a function of time.

2. The method of claim 1, wherein the antenna modules are compatible with 5G wireless communications standards.

3. The method of claim 1, wherein the antenna modules include one or both of patch and dipole antennas.

4. The method of claim 1, wherein the reflective object is one or more of a hand or other appendage of a user, or a hand held object.

5. The method of claim 1, wherein the motion of the anatomical feature is related to one or both of respiration and heartbeat and the biometric monitoring includes monitoring one or both of the respiration and the heartbeat.

6. The method of claim 1, wherein the performing one or both of gesture recognition and biometric monitoring includes transmitting a low power signal from the at least one transmit antenna and the received H-polarized signals and received V-polarized signals result from cross coupling between the transmit antenna and the receive antenna.

7. The method of claim 6, wherein power of the low power signal is not greater than 5 milliwatts.

8. The method of claim 6, wherein the low power signal is synchronized to occur only within random access channel slots.

9. The method of claim 6, wherein the low power signal is transmitted at a duty cycle of less than 0.01%.

10. The method of claim 9, wherein the low power signal is periodically transmitted during intervals approximately 100 msec apart, each interval having a duration of less than 10 microseconds.

11. An apparatus comprising:
processor and an electronic device having a wireless communications capability using beamforming techniques and including a plurality of millimeter wave antenna modules, each module including at least one transmit antenna and at least one receive antenna, operable in one or more frequency ranges not less than 20 GHz, the receive antenna coupled with a first branch configured to receive H-polarized signals and a second branch configured to receive V-polarized signals; and
the processor configured to perform one or both of gesture recognition and biometric monitoring with the electronic device by detecting a presence and motion of a reflective object or anatomical feature by determining a relationship of received H-polarized signals and received V-polarized signals as a function of time.

12. The apparatus of claim 11, wherein the antenna modules are compatible with 5G wireless communications standards.

13. The apparatus of claim 11, wherein the antenna modules include one or both of patch and dipole antennas.

14. The apparatus of claim 11, wherein the reflective object is one or more of a hand or other appendage of a user, or a hand held object.

15. The apparatus of claim 11, wherein the motion of the anatomical feature is related to one or both of respiration and heartbeat and the biometric monitoring includes monitoring one or both of the respiration and the heartbeat.

16. The apparatus of claim 11, wherein the received H-polarized signals and received V-polarized signals result from cross coupling, of a low power signal transmitted from the at least one transmit antenna, between the transmit antenna and the receive antenna.

17. The apparatus of claim 16, wherein power of the low power signal is not greater than 5 milliwatts.

18. The apparatus of claim 16, wherein the low power signal is synchronized to occur only within random access channel slots.

19. The apparatus of claim 16, wherein the low power signal is transmitted at a duty cycle of less than 0.01%.

20. The apparatus of claim 19, wherein the low power signal is periodically transmitted during intervals approximately 100 msec apart, each interval having a duration of less than 10 microseconds.

21. A non-transitory computer readable medium storing program code to be executed by a processor, the program code comprising instructions configured to cause the processor to:
perform one or both of gesture recognition and biometric monitoring with an electronic device, the electronic device having a wireless communications capability using beamforming techniques and including a plurality of millimeter wave antenna modules, each module including at least one transmit antenna and at least one receive antenna, operable in one or more frequency ranges not less than 20 GHz, the receive antenna coupled with a first branch configured to receive H-polarized signals and a second branch configured to receive V-polarized signals; wherein:
the processor detects a presence and motion of a reflective object or anatomical feature by determining a relationship of received H-polarized signals and received V-polarized signals for two or more receive antennas as a function of time.

22. The computer readable medium of claim 21, wherein the reflective object is one or more of a hand or other appendage of a user, or a hand held object.

23. The computer readable medium of claim 21, wherein the motion of the anatomical feature is related to one or both of respiration and heartbeat and the biometric monitoring includes monitoring one or both of the respiration and the heartbeat.

24. The computer readable medium of claim 21, wherein the received H-polarized signals and received V-polarized signals result from cross coupling, of a low power signal transmitted from the at least one transmit antenna, between the transmit antenna and the receive antenna.

25. The computer readable medium of claim 24, wherein power of the low power signal is not greater than 5 milliwatts.

26. The computer readable medium of claim 24, wherein the low power signal is transmitted at a duty cycle of less than 0.01%.

27. The computer readable medium of claim 24, wherein the low power signal is synchronized to occur only within random access channel slots.

28. An apparatus comprising:
an electronic device having a wireless communications capability using beamforming techniques and including a plurality of millimeter wave antenna modules, each module including at least one transmit antenna and at least one receive antenna, operable in one or more frequency ranges not less than 20 GHz, the receive antenna coupled with a first branch configured to receive H-polarized signals and a second branch configured to receive V-polarized signals; and
means for performing one or both of gesture recognition and biometric monitoring with the electronic device by detecting a presence and motion of a reflective object or anatomical feature by determining a relationship of received H-polarized signals and received V-polarized signals as a function of time.

29. The apparatus of claim 28, wherein the received H-polarized signals and received V-polarized signals result from cross coupling, of a low power signal transmitted from the at least one transmit antenna, between the transmit antenna and the receive antenna.

30. The apparatus of claim 29, wherein power of the low power signal is not greater than 5 milliwatts and the low power signal is synchronized to occur only within random access channel slots.

* * * * *